(12) United States Patent
Hutterer et al.

(10) Patent No.: US 11,497,460 B2
(45) Date of Patent: Nov. 15, 2022

(54) METHOD AND APPARATUS FOR DOSE MEASUREMENT IN AN X-RAY DEVICE

(71) Applicant: Siemens Healthcare GmbH, Erlangen (DE)

(72) Inventors: Albert Hutterer, Wetterfeld (DE); Jaroslaw Iwicki, Pressath (DE); Stephan Kreuzer, Kulmain (DE); Thomas Weber, Hausen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 17/224,352

(22) Filed: Apr. 7, 2021

(65) Prior Publication Data
US 2021/0315536 A1 Oct. 14, 2021

(30) Foreign Application Priority Data
Apr. 14, 2020 (DE) .................. 10 2020 204 673.5

(51) Int. Cl.
*A61B 6/00* (2006.01)
*G01T 1/02* (2006.01)

(52) U.S. Cl.
CPC ............. *A61B 6/58* (2013.01); *A61B 6/542* (2013.01); *G01T 1/023* (2013.01)

(58) Field of Classification Search
None
See application file for complete search history.

(56) References Cited

U.S. PATENT DOCUMENTS

| | | | |
|---|---|---|---|
| 6,330,299 B1 | 12/2001 | Curtis et al. | |
| 10,525,285 B1* | 1/2020 | Friedman | .................. G01T 1/40 |
| 2005/0226376 A1* | 10/2005 | Yun | ........................ G01T 1/2018 |
| | | | 378/62 |
| 2007/0036272 A1 | 2/2007 | Johansson et al. | |
| 2007/0181815 A1* | 8/2007 | Ebstein | .................. G01T 1/023 |
| | | | 250/370.11 |

FOREIGN PATENT DOCUMENTS

| | | |
|---|---|---|
| DE | 102005036514 A1 | 2/2007 |
| DE | 102010034680 A1 | 3/2012 |
| DE | 102006034348 B4 | 11/2015 |

(Continued)

OTHER PUBLICATIONS

VacuTec: "Radiation Measuring Technology in Medicine"; URL:https://www.vacutec-gmbh.de/en/products/medical.htm.

(Continued)

*Primary Examiner* — Hoon K Song
(74) *Attorney, Agent, or Firm* — Harness, Dickey & Pierce, P.L.C.

(57) ABSTRACT

An apparatus, for dose measurement designed for use in an x-ray device, is disclosed. In an embodiment, the apparatus includes a mirror element designed to inject a light field into an x-ray beam penetrating through the mirror element; and a measuring device to measure radiation-induced changes to a carrier material. The carrier material is part of the mirror element and/or another component of the apparatus, which lies in the radiation field of the x-ray device when used normally in an x-ray device. A corresponding method for dose measurement and to an x-ray device is also disclosed.

25 Claims, 2 Drawing Sheets

(56) References Cited

FOREIGN PATENT DOCUMENTS

EP          3858241  A1    8/2021
WO    WO 2014033112  A2    3/2014

OTHER PUBLICATIONS

Oppelt, Arnulf: Automatic fluoroscopy control, in: Imaging Systems for Medical Diagnostics, ISBN: 3-89578-226-2, pp. 312.
Szeifert, Karl-Heinz: "Basiswissen—Ionisationskammer und Ionendosis, Das Dosisflächenprodukt"; radiologiejtechnologie & mta-r.de; Jul. 5, 2019; URL: https://www.mta-r.de/blog/ionisationskammer-und-ionendosis.
German Office Action for German Patent Application No. 102020204673.5 dated Jan. 18, 2021.

\* cited by examiner

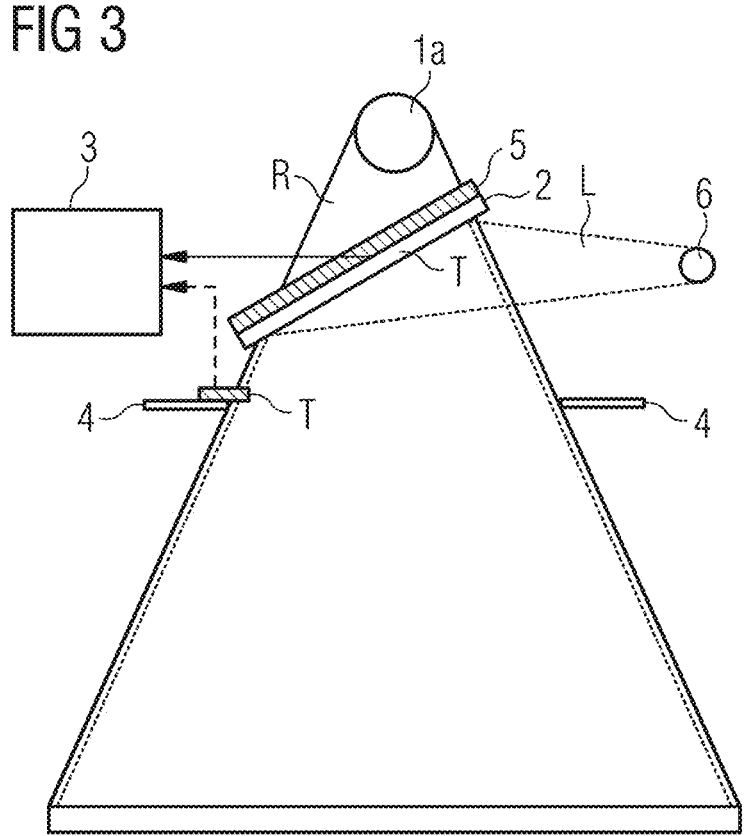
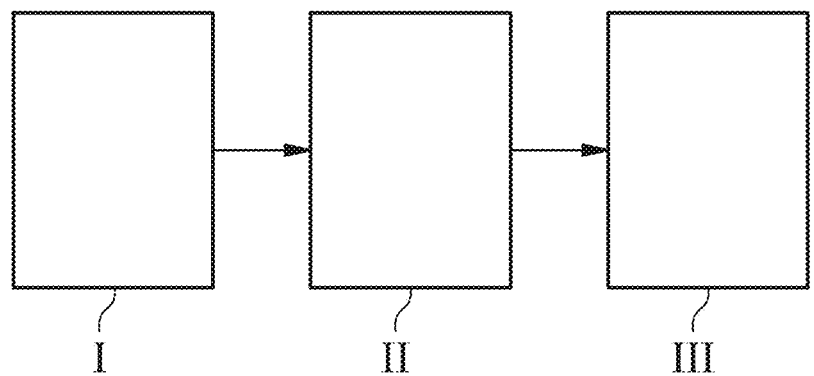

METHOD AND APPARATUS FOR DOSE MEASUREMENT IN AN X-RAY DEVICE

PRIORITY STATEMENT

The present application hereby claims priority under 35 U.S.C. § 119 to German patent application number DE 102020204673.5 filed Apr. 14, 2020, the entire contents of which are hereby incorporated herein by reference.

FIELD

Example embodiments of the invention generally relate to a method and an apparatus for dose measurement designed for use in an x-ray device, in particular an x-ray collimator with an integrated dose measuring system.

BACKGROUND

In x-ray diagnostics and intervention, it is necessary to monitor the radiation dose applied to a patient. For this purpose the dose to which the patient is exposed must be determined; this is achieved by the dose rate or the dose area product being measured or calculated in the area in front of the patient. This is prescribed as standard for indirect radiography, for instance.

The problem is currently resolved in that an ionization chamber is installed directly adjoining the x-ray collimator, said ionization chamber measuring the integral dose over the area (Dose Area Product (DAP)). Alternatively, the DAP can also be calculated from the generator parameters, such as inter alia tube voltage, tube current and radiation duration (see e.g. U.S. Pat. No. 6,330,299).

SUMMARY

The inventors discovered that both methods described above have disadvantages. A direct measurement of the dose is expensive and requires a considerable amount of additional space. A calculation is prone to miscalculations since to some extent simple assumptions about the pulse shapes have to be used. Furthermore, a calculation is not real-time capable, and can therefore not determine the current dose rate or DAP rate at the relevant point in time.

At least one embodiment of the present invention specifies an alternative, more convenient method and a corresponding apparatus for dose measurement, with which the afore-described disadvantages are avoided and in particular a simple, cost-effective and timely dose measurement is possible.

Embodiments are directed to an apparatus, a method and an x-ray device.

At least one embodiment is directed to an apparatus for dose measurement designed for use in an x-ray device, comprising:

a mirror element to inject a light field into an x-ray beam penetrating through the mirror element;

a measuring device to measure radiation-induced changes to a carrier material, the carrier material being part of at least one of the mirror element and another component of the apparatus, lying in the radiation field of the x-ray device when used in the x-ray device.

At least one embodiment is directed to a method for dose measurement by an x-ray device, comprising:

emitting an x-ray beam with an x-ray device; and measuring radiation-induced changes to a carrier material of an apparatus for dose measurement, for use in the x-ray device, the carrier material being part of at least one of a mirror element and another component of the apparatus, lying in a radiation field of the x-ray device when used in the x-ray device.

At least one embodiment is directed to an x-ray device, preferably a radiography device or a fluoroscopy device, in particular an x-ray collimator, comprising:

the apparatus of an embodiment, wherein the x-ray device is designed to inject a light field into an emitted x-ray beam.

BRIEF DESCRIPTION OF THE DRAWINGS

The invention is explained in more detail again below with reference to the appended figures on the basis of example embodiments. In the various figures, the same components are identified with identical reference signs. The figures are generally not true to scale and schematic.

In the drawings:

FIG. 3 shows a schematic representation of an example embodiment of the inventive apparatus, FIG. 4 shows a flow chart for a possible course of an example embodiment of an inventive method,

DETAILED DESCRIPTION OF THE EXAMPLE EMBODIMENTS

Figure 1:
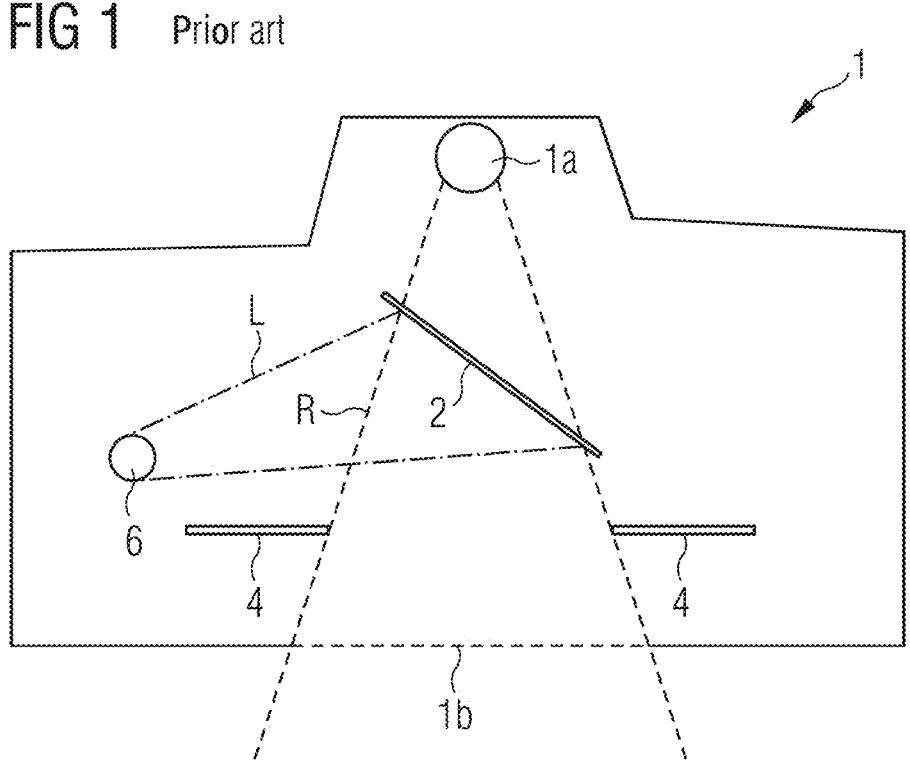
FIG. 1 shows a representation of a collimator according to the prior art.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/ DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes;

etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The inventive apparatus of at least one embodiment is used for dose measurement and is designed for use in an x-ray device, e.g. a radiography device or a fluoroscopy device or an x-ray collimator. In an x-ray device an advantageous application is equipped with a mirror for injecting a light field into an emitted x-ray beam or with a radiation-limiting component (e.g. a collimator) and optics for visually identifying the x-ray radiation area.

A light field which is produced with the aid of a lamp or an LED is used in many collimators. In most cases the light field is embedded into the x-ray beam by way of a mirror which is transparent for x-ray radiation.

In at least one embodiment, the apparatus comprises at least a mirror element, which is designed to inject a light field into an x-ray beam penetrating through the mirror element.

Such mirror elements are known, generally comprise mirrored glass, e.g. borofloat glass, which has been coated with aluminum and often has a silicon oxide protective layer, and are used e.g. in x-ray collimators to visually display the measuring range. The inventors identified that the mirror element can be used to determine the dose, since it is penetrated wholly by the x-ray radiation. They identified the same for other materials in the radiation path, e.g. collimators.

In at least one embodiment, the apparatus further comprises at least:

a measuring unit designed to measure radiation-induced changes to a carrier material.

The carrier material is part of the mirror element and/or another component of the apparatus, which, during normal use in an x-ray device, lies in the radiation field of the x-ray device.

A collimator can be another such component of the apparatus in at least one embodiment, for instance. Changes are therefore measured, for instance, by means of heating or ionization within the mirror element or a collimator sheet (a collimation-limiting disk).

It should be noted here that even though the mirror element has to be part of the apparatus in order to achieve a deflection of the light field for visual monitoring purposes, the measurements for dosage do not always have to be carried out on this mirror element, but can instead also be carried out on a collimator plate, for instance.

Since x-ray radiation is ionizing, changes can be measured through the ionization within the mirror element or a collimator plate, for instance. In this regard, electrical properties such as the electrical conductivity or the capacitance (particularly if a capacitive layer is disposed on the mirror element or a collimator plate) can be determined as a function of the ionization.

For instance, the change in the electrical resistance of the carrier material as a result of the x-ray radiation can be determined by means of a Thomson bridge or Kelvin bridge, in which the carrier material is inserted into a corresponding circuit as an unknown resistor. Linking the resistance to a dose can then take place by calibrating the circuit with known dose values and measuring the respective resistances of the carrier material.

The use of the mirror element for dose measurement does not require additional parts in the radiation path and at the same time reduces the scatter radiation which is produced by use of a DAP chamber. Compared with an approximation of the values, direct measurement of the dose is much more accurate.

It is also possible, however, to use a mirror element or another component, on which a scintillating material is located. Similarly to the mode of operation of an indirectly converting x-ray detector, the dose rate can then be determined by measuring the light quantity emitted by a scintillator. At present the image amplifier (IA) would regulate the brightness or the exposure of a film so that the quantity of light produced at the outlet window of the BV would be distributed across a semi-transparent mirror and would measure the intensity of a small part by means of a photomultiplier (cf. extract from Oppelt et al.; page 312 "Automatic fluoroscopy control"). The signal thus generated is, on the one hand, proportional to the dose (after calibration) and is, on the other hand, present in real time.

The inventive method of at least one embodiment for dose measurement of the dose output by an x-ray device in a measuring range comprises:

providing an x-ray device with an embodiment of the inventive apparatus.

The x-ray device comprises, in addition to the elements which are required for an x-ray measurement, a mirror element for injecting a light field into the x-ray beam and a measuring unit as described above.

In at least one embodiment, the apparatus further comprises at least:

emitting an x-ray beam with the x-ray device. This x-ray beam is naturally aligned so that it strikes the afore-cited carrier material so that an inventive measurement is actually possible.

In at least one embodiment, the apparatus further comprises at least:

measuring radiation-induced changes to a carrier material of the apparatus, wherein the carrier material is part of the mirror element and/or another component of the apparatus, which, during normal use in an x-ray device, (as said above), is disposed in the radiation field of the x-ray device.

An inventive x-ray device of at least one embodiment comprises an inventive apparatus of at least one embodiment and/or is designed to carry out an inventive method of at least one embodiment, wherein the x-ray device is designed to inject a light field into an emitted x-ray beam. The x-ray device is or comprises preferably a radiography device or a fluoroscopy device.

In particular, the x-ray device is or comprises an x-ray collimator.

Further particularly advantageous embodiments and developments of the invention are given in the claims and the subsequent description, wherein the claims of a claims category are also developed in a similar way to the claims and passages of the description relating to another claim category and in particular also individual features of different example embodiments or variants can also be combined to create new example embodiments or variants.

According to a preferred apparatus, the mirror element has the carrier material. The carrier material is preferably mirrored here and is also preferably used as a mirror. Alternatively, the carrier material is preferably applied to a mirror, in other words the mirror element consists of a mirror and applied carrier material (and possibly further components). It is advantageous if the measurement is carried out near to the focus (on the rear of the mirror or mirror element).

Here the mirror surface is on the side which is remote from the focus.

A preferred apparatus of an embodiment comprises a collimator sheet as another component, wherein the collimator sheet has the carrier material. Here the carrier material is preferably attached at least to that edge of the collimator sheet which is used for collimation of an x-ray beam during normal use. Those areas of a collimator sheet which, with any reasonably possible position of the collimator sheet, are located in the radiation field, are the preferred areas for applying the carrier material. The material of the collimator sheet is preferably considered to be a carrier material.

According to a preferred apparatus of an embodiment, the carrier material changes its electrical properties when x-ray radiation passes through. In addition or alternatively, the carrier material comprises a scintillator material, preferably a scintillating plastic or gadolinium oxysulfide, calcium tungstate, cesium iodide or polyvinyl toluene. The scintillator material converts one part of the x-ray radiation into visible light. The carrier material is therefore in particular a scintillation material and/or a material, the electrical properties of which change during radiation.

According to a preferred apparatus of an embodiment, the measuring unit is designed to measure radiation-induced changes of the carrier material. It is furthermore preferably connected directly or via a signal conductor to the carrier material for this measurement.

A suitable signal conductor depends on the type of measurement. If electrical properties are measured, the signal conductor is preferably electrically conductive (e.g. a current cable). If thermal properties are measured, the signal conductor is preferably temperature-conductive (e.g. a thermal conductor in particular made from metal). If optical properties are measured (e.g. scintillation light), the signal conductor is preferably a light conductor (e.g. a glass fiber).

According to a preferred apparatus of an embodiment, within the scope of measurement, the measuring unit determines changes to electrical properties of the mirror element, preferably the electrical conductivity and/or the capacitance. Here the mirror element particularly preferably has a capacitive layer, and comprises in particular a dielectric.

According to a preferred apparatus of an embodiment, the measuring unit is designed to measure light, which is generated in a carrier material when x-ray radiation passes through, wherein the mirror element particularly preferably has a scintillating carrier material. The mirror element, which deflects the light field used for collimation in the patient direction, is preferably coated with a scintillator on the side which faces the x-ray emitter.

The intensity of the generated light is best detected by means of a light-sensitive component. This can be e.g. a photomultiplier. However, one or more photodiodes (preferably organic photodiodes) or photoresistors are advantageously also used to measure the light intensity.

According to a preferred apparatus of an embodiment, one element of the measuring unit is disposed in a carrier material on the mirror element, preferably in the form of a dose measuring apparatus for measuring a radiation dose. This dose measuring apparatus preferably comprises a dose measuring field, which has in particular pixels which can be connected together particularly preferably to form at least one relevant measuring surface.

For this purpose reference is made to publication WO 2014/033112, the entire contents of which are hereby incorporated herein by reference.

According to a preferred apparatus of an embodiment, the measuring unit is located outside of the area through which an x-ray beam passes during normal use of the apparatus. This is advantageous since as a result the homogeneity of the radiation field is not interrupted. To this end the light-sensitive component should not be located in the radiation path.

According to a preferred apparatus of an embodiment, a measurement is carried out by the measuring unit on a side edge of the mirror element or on the side edge of a carrier material, preferably at an angle of greater than 30°, in particular greater than 60°, particularly preferably of 90°, with respect to the primary beam of the radiation source. This is likewise advantageous since as a result the homogeneity of the radiation field is not disturbed.

According to a preferred apparatus of an embodiment, the measuring unit is an x-ray detector, in particular a one-pixel x-ray detector, which is arranged so that it can measure scatter radiation on the mirror element and/or the other component of the apparatus during normal use of the apparatus. In particular, it is arranged laterally. Here the x-ray detector is preferably indirectly or directly converting and/or energy-discriminating and/or photon-counting.

According to a preferred method of an embodiment, calibration takes place before a measurement so that with different intensities and/or energies of the x-ray beam, values are measured with the measuring unit of the apparatus and these values are linked to the respective intensities and/or energies of the x-ray beam via a data link, so that a calibration table and/or calibration function is produced.

According to a preferred method of an embodiment, the emission of the x-ray radiation of the x-ray apparatus is regulated on the basis of the measurement. The regulation is preferably carried out here so that it is regulated to a constant, in particular predetermined, measured value.

According to a preferred method of an embodiment, the results of the dose measurement are used to regulate the x-ray device. An x-ray source of the x-ray device is preferably regulated here on the basis of the measured dose. To this end, the inventive method is particularly advantageous, because the measurement takes place "in real time".

Since the intensity of scattered radiation of the x-ray radiation in a spatial angle is proportional to the intensity of the primary radiation, the dose can also be concluded herefrom. A radiation-induced change to a carrier material is therefore preferably measured, which is located in the area of the scatter radiation of the x-ray beam.

A great advantage of an embodiment of the invention is that it can be implemented in a space-saving manner in already existing devices.

FIG. 1 shows a collimator 1 as an example of an x-ray device 1 according to the prior art. The detailed design is known to the person skilled in the art. An x-ray source 1a is arranged at the top, which, during operation, generates an x-ray beam R (see FIG. 2), which passes from the top through the mirror element 2 out of the outlet window 1b. The area of the x-ray beam is bounded by collimator plates 4, which can generally be adjusted.

The mirror element 2 is used to deflect a light field F (see FIG. 2), which is generated by a light source 6 (e.g. an LED) and deflected through the mirror element 2 so that in accordance with the x-ray beam R it likewise passes out of the outlet window 1b. The light field F is used as a visual marker for the irradiated area.

Figure 2:
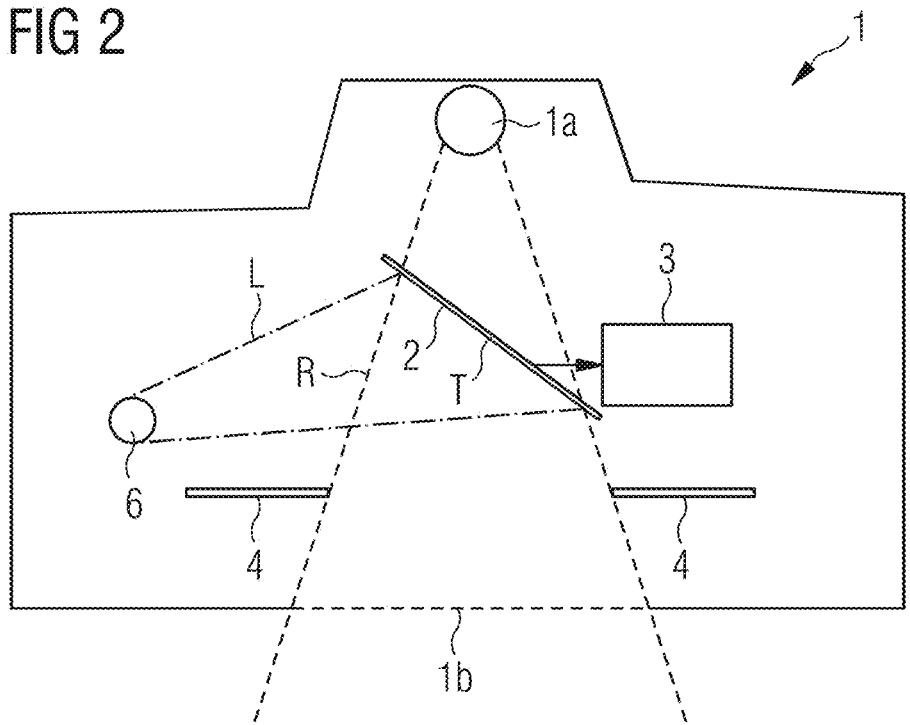
FIG. 2 shows a representation of an example embodiment of an inventive collimator.

FIG. 2 shows an example embodiment of a collimator 1 according to FIG. 1, which has been changed in accordance with the invention. Contrary to the prior art, the collimator 1 comprises a measuring unit 3, which is designed to measure radiation-induced changes to a carrier material T. The carrier material is in this case e.g. part of the mirror element 2, e.g. a mirrored plate. The arrow indicates that the measuring unit 3 measures a property of the mirror element 2, which is changed by the radiation. The arrow can also be representative of a signal conductor.

FIG. 3 shows an inventive apparatus, which can be contained e.g. in the collimator 1 in FIG. 2. An x-ray source 1a is also arranged at the top here, which, during operation, generates an x-ray beam R which passes from the top through the mirror element 2. The area of the x-ray beam R is bounded by collimator plates 4. A light field F which is deflected by the mirror element 2 so that it matches the x-ray beam R is generated by means of a light source 6.

Both the mirror unit 2 and also a collimator plate 4 comprise a carrier material T, the properties of which are changed by the x-ray beam R. The electrical conductivity or the capacitance can change, for instance, or the carrier material T is a scintillator which emits light when x-ray radiation R passes through.

A measuring unit 3, which is designed to measure radiation-induced changes to a carrier material T, measures the changes of the carrier material T. The continuous arrow indicates that the mirror element 2 is used here for measurement purposes, the dashed arrow indicates that the collimator plate 4 can also be used as an alternative or in addition for measurement purposes.

FIG. 4 shows a flow chart for a possible course of an inventive method for dose measurement of an x-ray device 1.

In step I, an x-ray device 1 is provided with an inventive apparatus, as e.g. shown in FIG. 2.

In step II, an x-ray beam R is emitted by the x-ray source 1a of the x-ray device 1.

In step III, radiation-induced changes to a carrier material T of the apparatus are measured, wherein the carrier material T is part of the mirror element 2 and/or another component of the apparatus (see e.g. FIG. 3).

Finally, it should again be noted that the apparatuses described above in detail and the x-ray device 1 disclosed are merely example embodiments which can be modified by a person skilled in the art in a wide variety of ways without departing from the scope of the invention. Furthermore, the use of the indefinite article "a" or "an" does not preclude the possibility that the relevant features can also be present plurally. Similarly, the expressions "unit" and "module" do not preclude the components in question from consisting of a plurality of cooperating partial components which can also be spatially distributed.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. An apparatus for dose measurement designed for use in an x-ray device, comprising:
   a mirror element to inject a light field into an x-ray beam penetrating through the mirror element; and
   a measuring device to measure radiation-induced changes to a carrier material, the carrier material being part of at least one of the mirror element and another component of the apparatus, lying in a radiation field of the x-ray device when used in the x-ray device.

2. The apparatus of claim 1, wherein the mirror element includes the carrier material, the carrier material being mirrored and used as a mirror, or the carrier material being applied to a mirror.

3. The apparatus of claim 1, further comprising:
   a collimator sheet, the collimator sheet including the carrier material.

4. The apparatus of claim 1, wherein at least one of
   the carrier material is configured to change its electrical properties when x-ray radiation passes through and
   the carrier material includes a scintillator material.

5. The apparatus of claim 2, wherein the measuring device is designed to measure radiation-induced changes of the carrier material.

6. The apparatus of claim 1, wherein, within a scope of the dose measurement, the measuring device is configured to determine changes to electrical properties of the mirror element.

7. The apparatus of claim 1, wherein the measuring device is designed to measure light, generated in a carrier material when x-ray radiation passes through.

8. The apparatus of claim 1, wherein an element of the measuring device is present in a carrier material on the mirror element.

9. The apparatus of claim 1, wherein the measuring device is located outside of an area through which an x-ray beam passes during use of the apparatus.

10. The apparatus of claim 1, wherein a measurement by the measuring device takes place on a side edge of the mirror element or on a side edge of a carrier material.

11. The apparatus of claim 1, wherein the measuring device is an x-ray detector, arranged to, during use of the apparatus, to measure scatter radiation on at least one of the mirror element and another component of the apparatus.

12. A method for dose measurement by an x-ray device, comprising:
emitting an x-ray beam with an x-ray device; and
measuring radiation-induced changes to a carrier material of an apparatus for dose measurement, for use in the x-ray device, the carrier material being part of at least one of a mirror element and another component of the apparatus, lying in a radiation field of the x-ray device when used in the x-ray device.

13. The method of claim 12, wherein a calibration takes place before a measurement, the method further comprising:
measuring, with different at least one of intensities and energies of the x-ray beam, values via a measuring device of the apparatus, the values being connected to the respective at least one of intensities and energies of the x-ray beam via a data link so that at least one of a calibration table and a calibration function is produced.

14. The method of claim 12, further comprising:
regulating emission of x-ray radiation of the x-ray device based upon the measuring of the radiation-induced changes to the carrier material.

15. An x-ray device, preferably a radiography device or a fluoroscopy device, in particular an x-ray collimator, comprising:
the apparatus of claim 1, wherein the x-ray device is designed to inject a light field into an emitted x-ray beam.

16. The apparatus of claim 2, further comprising:
a collimator sheet, the collimator sheet including the carrier material.

17. The apparatus of claim 3, wherein the carrier material being attached at least to an edge of the collimator sheet that is used for collimation of an x-ray beam during normal use.

18. The apparatus of claim 4, wherein the carrier material includes a scintillator material including a scintillating plastic or gadolinium oxysulfide, calcium tungstate, cesium iodide or polyvinyl toluene.

19. The apparatus of claim 5, wherein the measuring device is connected directly or via a signal conductor to the carrier material for this measurement.

20. The apparatus of claim 6, wherein, within a scope of the dose measurement, the measuring device is configured to determine at least one of electrical conductivity and capacitance.

21. The apparatus of claim 20, wherein the mirror element includes a capacitive layer.

22. The apparatus of claim 7, wherein the mirror element includes a scintillating carrier material.

23. The apparatus of claim 8, wherein the element of the measuring device, present in the carrier material on the mirror element, is a dose measuring apparatus for measuring a radiation dose with a dose measuring field, including pixels, connectable together, to form at least one relevant measuring surface.

24. The apparatus of claim 11, wherein the x-ray detector is at least one of
indirectly or directly converting and
energy-discriminating or photon-counting.

25. The method of claim 14, wherein the regulating of the emission of x-ray radiation of the x-ray device takes place to regulate the emission to a constant value.

* * * * *